United States Patent [19]
Bewart et al.

[11] Patent Number: 6,114,591
[45] Date of Patent: Sep. 5, 2000

[54] PROCESS FOR PREPARING HIGHLY CHLORINATED PARAFFINS

[75] Inventors: Dietmar Bewart, Gersthofen; Walter Freyer, Stadtbergen, both of Germany

[73] Assignee: Dover Chemical Corporation, Dover, Ohio

[21] Appl. No.: 09/115,349

[22] Filed: Jul. 14, 1998

Related U.S. Application Data

[63] Continuation-in-part of application No. 08/336,470, Nov. 9, 1994.

[51] Int. Cl.⁷ .............................. C07C 17/10; C07C 17/00
[52] U.S. Cl. ....................................... 570/252; 204/157.95
[58] Field of Search ........................ 570/252; 204/157.95

[56] References Cited

U.S. PATENT DOCUMENTS 3,948,741  4/1976  McCoy .

FOREIGN PATENT DOCUMENTS

| | | |
|---|---|---|
| 1443892 | 12/1968 | Germany . |
| 1905923 | 1/1970 | Germany . |
| 2150599 | 12/1974 | Germany . |
| 1114612 | 5/1968 | United Kingdom . |
| 1327268 | 8/1973 | United Kingdom . |

*Primary Examiner*—Alan Siegel
*Attorney, Agent, or Firm*—Oldham & Oldham Co., L.P.A,.

[57] ABSTRACT

The chlorination of paraffins is carried out in the presence of water and in the absence of an organic solvent. In this way, it is possible to prepare highly chlorinated paraffins in a simple manner. The presence of hydrochloric acid even at high temperatures, has no deleterious effect on the quality of the product. The separation of the chloroparaffin from the hydrochloric acid is very good. An emulsion layer which hinders the transport of the chloroparaffin into downstream equipment does not occur.

20 Claims, No Drawings

PROCESS FOR PREPARING HIGHLY CHLORINATED PARAFFINS

This application is a CIP of 08/336,470 filed Nov. 9, 1994.

TECHNICAL FIELD

This invention described herein pertains generally to the chlorination of paraffins in the presence of water and in the absence of an organic solvent. In this way, it is possible to prepare highly chlorinated paraffins in a simple manner. The conversion to the chloroparaffins is carried out using an essentially stoichiometric amount of liquefied chlorine in the presence of a free-radical-forming catalyst, such as, for example, organic peroxides, or under the action of ultraviolet rays, X-rays, etc.

BACKGROUND OF THE INVENTION

In the Prior Art, the preparation of chlorinated hydrocarbons containing from 14 to 40 carbon atoms and having a chlorine content of more than 60%, is carried out in an organic solvent, since the melt viscosity of the chlorinated paraffins formed is very high and chlorine exchange between the gaseous and the liquid phase no longer takes place normally. The solvent used is principally carbon tetrachloride, although other organic solvents such as halogenated $C_1$ or $C_2$ hydrocarbons are used in the paraffin chlorination reaction, examples of which would include chloroform, pentachloroethane, perchloroethylene, 1,1,1-trichloroethane, 1,1,2-trichloroethane, and ethylene dichloride. However, with increasing environmental concerns regarding cancer and ozone layer depletion, the use of these organic solvents is not preferred today. The use of chlorofluorocarbons is also described in the literature as in German patent DE 2,150,599.

German patent DE 1,443,892 or its British equivalent (GB 1,114,612) teaches using an excess of chlorine in the reaction, which under pressure, will function in the same manner as using carbon tetrachloride as a solvent to dissolve the chlorinated material and promote the chlorine exchange reaction. This excess chlorine must still be removed with the attendant problems associated with removal of any organic solvent, requiring heating to a high temperature followed by vacuum stripping.

German patent DE 1,905,923, focuses on achieving a selective monochloroparaffin formation. For a $C_{14}$ paraffin resin, this is a chlorination level of approximately 18%, while for a $C_{40}$ paraffin resin, this is a chlorination level of approximately 6%. It has been generally known that it is possible to chlorinate these types resins up to as high a chlorination level as 50%, with or without any solvent.

The instant invention overcomes the prior art problems by essentially reacting a stoichiometric amount of chlorine with the paraffin wax. In that manner, there is no residual chlorine which will act as an organic solvent in excess, and which will need to be removed later. Additionally, there is no emulsion layer between the chlorinated paraffin layer and the aqueous layer, which also increases the final product isolation costs.

SUMMARY OF THE INVENTION

In accordance with the present invention, there is provided a method for the preparation of highly chlorinated paraffins having a chlorine content of more than 60% by weight, at a temperature of from 75–140° C. and a pressure of up to 10 bar by reacting a paraffins having from 14 to 40 carbon atoms with liquid chlorine, wherein the reaction is carried out in the presence of water and the chlorine reacts essentially completely and without organic solvents being present.

Since chlorinated hydrocarbons have environmental and health concerns, and require particular expertise and expense in handling, it is an object of this invention to reduce their amount in the production of chlorinated paraffins to the greatest extent possible.

It has also been discovered that it is possible to prepare highly chlorinated paraffins in the absence of an organic solvent.

These and other objects of this invention will be evident when viewed in light of the drawings, detailed description, and appended claims.

DETAILED DESCRIPTION OF THE INVENTION

The best mode for carrying out the invention will now be described for the purposes of illustrating the best mode known to the applicant at the time. The examples are illustrative only and not meant to limit the invention, as measured by the scope and spirit of the claims.

In this application, starting materials are saturated or unsaturated hydrocarbons having from 14 to 40, preferably from 17 to 24, carbon atoms These hydrocarbons may already contain chlorine atoms and therefore be considered to have been prechlorinated. These materials also include various types of hydrocarbons, for example, n-paraffins, α-olefins, etc.

The chlorination is effected by means of liquid chlorine. The pressure in the reaction vessel is from 0 to up to 10 bar, preferably from 2 to 6 bar. The reaction temperature is from 75 to 140° C., preferably from 80 to 105° C.

The reaction is carried out in the presence of a free-radical forming catalyst. The catalyst will typically contain bonds such as —COOC—, —COOOC—, and —CNNC—which dissociate to form free radicals. Preferably, the free-radical forming catalyst comprises an azo compound, for example an azonitrile such as α,α-azobisisobutyronitrile, or an organo peroxide such as benzoyl peroxide or dilauroyl peroxide or an organo hydroperoxide. Preference is given to using a,a-azobisisobutyronitrile or dilauroyl peroxide. However, it is possible to use free radicals which have been formed by the action of ultraviolet light or other ionizing radiation, e.g., X-rays.

The reaction of the paraffins with the chlorine is carried out in the presence of water which absorbs the hydrogen chloride formed during the reaction, or dilute hydrochloride acid.

The process of the invention can be carried out in various types of apparatii. Possible configurations include stirred reactors, falling film reactors, loop reactors, and bubble-column reactors to name a few. The essential point is that intensive mixing of the aqueous and organic phases is extremely desirable to effect the reaction in a preferred embodiment. Preference is given to using a stirred reactor with an impeller stirrer.

The process of the invention makes it possible to prepare highly chlorinated paraffins in a simple manner. It has been found that the presence of hydrochloric acid, even at the high temperatures, has no deleterious effect on the product quality. The separation of the chloroparaffin from the hydrochloric acid is very good under these conditions. An emulsion layer which inhibits the transport of the chloroparaffin into downstream equipment does not occur.

EXAMPLES

The following experiments were carried out in a stirred reactor of enameled steel having a volume of 8 m$^3$ and fitted with an impeller stirrer. The reaction mixture was stirred with the stirrer having 3 blades in association with deflectors, i.e., baffles. The chlorinator was provided with means by which the raw materials such as paraffin, water or dilute hydrochloric acid, the solvent and also the free radical initiator are fed into the reactor. A dip pipe was present for continuously feeding in liquid chlorine. In a preferred embodiment, the pipe advantageously dips into the reaction mixture and, if possible, ends below the level of the stirrer. In each experiment, the amount of water or hydrochloric acid was calculated in such a way that during chlorination, there was formed hydrochloric acid having a strength of from 29% (m/m) to 35% (m/m), so that it was not necessary to conduct away the hydrogen chloride formed in the chlorination. The chlorination unit contained pressure and temperature measuring devices for safety.

Comparative Example A (Prior Art)

A mixture of 730 kg of paraffin hydrocarbons having from 17 to 26 carbon atoms in the molecule, 1600 kg of carbon tetrachloride (40% m/m) based on the chloroparaffin prepared) and 3900 kg of water were reacted with 3570 kg of liquid chlorine in the presence of 0.3% of dilauroyl peroxide, based on the chloroparaffin prepared, at a temperature of from 84 to 1 03° C. The pressure increased up to 5.3 bar during the course of the chlorination. The desired amount of chlorine was introduced over a period of about hours, with the chlorine introduced having reacted completely, i.e., to more than 99.9% (m/m). After chlorination was complete, the stirrer was turned off and phase separation achieved within ten (10) minutes. The organic phase was drained to remove the solvent. The chloroparaffin had a chlorine content of 72% (m/m) with a yield of 2500 kg of solid chloroparaffin.

Comparative Example B

The chlorination was carried out in a manner similar to that described in Comparative Example A, except that chloroform was used in place of carbon tetrachloride and the amount of chlorine fed in was increased proportionately accounting for the differences in the chlorine content of chloroform in comparison to carbon tetrachloride. The chloroparaffin obtained had a chlorine content of about 72% (m/m) and phase separation was achieved within ten (10) minutes at a temperature from 84 to 102° C.

Comparative Example C

At otherwise constant amounts used, the experimental conditions were changed by reducing the amounts of carbon tetrachloride as a solvent to 1400 kg corresponding to 36% (m/m), based on the chloroparaffin prepared. A chlorination time of about 5.5 hours was used and a phase separation time of about 10 minutes at a temperature of from 84 to 102° C. was achieved with the preparation of 2500 kg of chloroparaffin having a chlorine content of 72% (m/m). The drainage time into the downstream equipment to remove the solvent was ten (10) minutes.

Comparative Example D

At otherwise constant amounts used, the experimental conditions were changed by reducing the amounts of carbon tetrachloride as the solvent to 900 kg corresponding to 26% (m/m), based on the chloroparaffin prepared. A chlorination time of about 5.5 hours was used and a phase separation time of 20 minutes at a temperature of 95° C. was achieved resulting in the preparation of 2500 kg of chloroparaffin having a chlorine content of about 72% (m/m). An emulsion layer was observed between the phases. The drainage of the product into the downstream equipment took 12 minutes and was only slightly hindered.

Comparative Example E

At otherwise constant amounts used, the experimental conditions were changed by reducing the amounts of carbon tetrachloride as the solvent to 600 kg corresponding to 19% (m/m) based on the chloroparaffin prepared. A chlorination time of about 5.5 hours as used and a phase separation time of 25 minutes at a temperature of 94° C. was achieved resulting in the preparation of 2500 kg of chloroparaffin having a chlorine content of about 72% (m/m). An emulsion layer was observe between the phases, this layer being present in significantly greater quantities than in Comparative Example D. The drainage time into the downstream equipment to remove the solvent was increased to 23 minutes.

Comparative Example F

At otherwise constant amounts used, the experimental conditions were further changed by reducing the amounts of tetrachloromethane to 300 kg corresponding to 11% (m/m), based on the chloroparaffin prepared. A chlorination time of about 7 hours was used and a phase separation of about 40 minutes at a temperature of 94° C. was achieved resulting in the preparation of 2500 kg of chloroparaffin having a chlorine content of about 72% (m/m). The drainage time into the downstream equipment for removing the solvent was increased to about 60 minutes. Owing to a thick emulsion layer between the two phases, the time for distilling off the solvent was considerably increased as a result of entrained hydrochloric acid.

Example #1

At otherwise constant amounts used, the experimental conditions were further changed by entirely omitting the solvent carbon tetrachloride or chloroform. At a chlorination time of about 7.5 hours and a phase separation time of about 30 minutes, which owing to the absence of an organic solvent, could be carried out at a temperature of 135° C., 2500 kg of chloroparaffin was again prepared. The phase separation was very good without signs of an emulsion layer. The hydrochloric acid phase was very clean and free of chloroparaffin flocs. The drainage time into the downstream apparatus was 55 minutes. Owing to the good phase separation, residual amounts of hydrochloric acid were quickly and completely removed from the chloroparaffin wax.

In a preferred embodiment and in order to achieve an acceptable chlorination time even without chlorinated organic solvents, the gap between the impeller stirrer and the bottom of the reactor has to be so small, and the diameter of the stirrer has to be so designed, that the chloroparaffin/ paraffin mixture drawn in is sufficiently well dispersed and intimately mixed wit the aqueous phase and the chlorine present. After the reaction was complete, the mixture was heated to a temperature of up to 140° C., to achieve satisfactory separation of the phases.

Example #2

In further experiments, under the same experimental conditions and with constant amounts used in a similar manner to Example #1, the paraffin hydrocarbon used was varied in terms of chain length distribution. In each case, after chlorination was complete, phase separation was achieved at temperatures up to 140° C., without an emulsion layer interfering with further work up being observed.

A summary of the data presented in the above examples is shown in Table I.

TABLE I

| Expt. | A | C | D | E | F | #1 |
|---|---|---|---|---|---|---|
| paraffin wax (kg) | 730 | 730 | 730 | 730 | 730 | 730 |
| CCl$_4$ (kg) | 1600 | 1400 | 900 | 600 | 300 | none |
| H$_2$O (kg) | 3900 | 3900 | 3900 | 3900 | 3900 | 3900 |
| Cl$_2$ (kg) | 3570 | 3570 | 3570 | 3570 | 3570 | 3570 |
| Temp (° C.) | 84–103 | 84–102 | 84–102 | 84–102 | 84–102 | 84–102 |
| Rx. Time (hrs) | 5 | 5.5 | 5.5 | 5.5 | 7 | 7.5 |
| Phase Sep. Time (min) | 10 | 10 | 20 | 25 | 40 | 30 |
| Drainage Time (min) | | 10 | 12 | 23 | 60 | 55 |
| Emulsion layer formed | | | YES | YES | YES | NO |

The significant differences in the Table lie in the reduced amounts of the carbon tetrachloride used up to the total elimination of the same in the last column, as well as the phase separation time with concurrent increase in drainage times. Based on the trend observed with Comparative Examples D–F, it would have been anticipated that even longer phase separation and drainage times would have been observed for the aqueous chlorination technology he instant invention. However, contrary to the expected trend, the separation and drainage times decreased as well as resulting in the elimination of the undesirable emulsion layer.

A further series of four experiments were performed to demonstrate the differences between chlorination processes of the prior art and that of the instant invention, the results of which are summarized in Table II.

Comparative Example #G (Solution Process)

In a reaction vessel, 100 parts of high melt unstabilized wax (melting point of 50° C.) were added, and heated to 60° C. An additional 300 parts of CHCl$_3$ were added and the mixture stirred for 30 minutes. Chlorine was introduced into the reactor and the chlorination reactor initiated by exposing the reaction mixture to light. The chlorination process was continued until the amount of chlorine in the product reached >70%. The reaction time was 30 hours. The reaction mixture was then degassed with nitrogen to remove dissolved gasses and 1% epoxide added as a stabilizer. The solvent was stripped to a maximum temperature of 150° C. with full vacuum. The product was then flaked and ground to give a free flowing powder.

Comparative Example H (Emulsion Process)

In a reaction vessel, 100 parts of high melt unstabilized wax (melting point of 50° C.) were added, and heated to 60° C. An additional 300 parts of CHCl$_3$ and 300 parts water were added and the mixture stirred for 30 minutes. Chlorine was introduced into the reactor and the chlorination reactor initiated by exposing the reaction mixture to light/peroxide. The chlorination process was continued until the amount of chlorine in the product reached >70%. The reaction time was 28 hours. The reaction mixture was then cooled to room temperature without stirring and the acidic layer was allowed to settle for one hour. The acid layer was then drained out while the organic layer was heated to remove residual acidic water and to remove dissolved gasses and 1% epoxide added as a stabilizer. The solvent was stripped to a maximum temperature of 150° C. with full vacuum. The product was then flaked and ground to give a free flowing powder.

Comparative Example I (Neat Process)

In a reaction vessel, 100 parts of high melt unstabilized wax (melting point of 50° C.) were added, and heated to 60° C. Chlorine was introduced into the reactor and the chlorination reaction initiated by exposing the reaction mixture to light. The reaction mixture was heated to 130–140° C. for further chlorination. The chlorination process was continued until the amount of chlorine in the product reached ~70%. The reaction time was 65 hours. The reaction mixture was then degassed with nitrogen to remove dissolved gasses and 1% epoxide added as a stabilizer. The product was then flaked and ground to give a free flowing powder.

Example #3 (Aqueous Process)

In a reaction vessel, 100 parts of high melt unstabilized wax (melting point of 50° C.) were added, and heated to 60° C. An additional 300 parts of water were added and the mixture stirred for 30 minutes. Chlorine was introduced into the reactor and the chlorination reactor initiated by exposing the reaction mixture to light/peroxide. The chlorination process was continued and the batch temperature was increased to 110° C. until the amount of chlorine in the product reached >70%. The reaction time was 55 hours. The reaction mixture was then degassed with nitrogen to remove dissolved gasses and the acidic layer was allowed to settle for one hour and drained out. A fresh layer of water was introduced at 110° C. to remove residual acidic water and to remove dissolved gasses. To the dry molten product solution, 1–3% epoxide was added as a stabilizer. The product was then flaked and ground to give a free flowing powder.

TABLE II

| | Experiment # | | | |
|---|---|---|---|---|
| Property | G | H | I | 3 |
| alpha color | 90 | 45 | 500 | 60 |
| softening point | 105° C. | 100–140° C. | <100° C. | 95° C. |
| % chlorine | 71% | 72% | 68% | 72% |
| CTC % | ~0.06% | ~0.06% | none | none |
| Thermal Stability | | | | |
| % HCl after 4 hr @ 175° C. | 0.1% | 0.02% | 0.2% | 0.1% |
| Heat Test @ 200° C. | pass | pass | fail | pass |

The color of the product was measured using a solution containing 15 grams of product in 100 ml of toluene. This sample solution was tested in Helliage Daylight colorimeter and the results reported in alpha units. The softening point was determined using ASTM E28–67, which is a measurement of the temperature at which a disk of the sample which is held within a horizontal ring, is forced downward 1 inch under the weight of a steel ball as the sample is heated at a prescribed rate in a glycerin bath. The residual carbon tetrachloride (CTC) was measured by gas chromatography using a head space sampler while the thermal stability test used a sample size of 20 grams which was subjected to 175° C. with the off gases collected for four hours in a known amount of NaOH solution. The resultant NaOH solution was back titrated with sulfuric acid solution using phenolphthalein as the indicator. The heat test involved placing ten grams of sample into test tubes with heating in a constant temperature hot oil bath at 200° C. The molten samples from each test tube were transferred into disks at 5, 10 and 15 minutes. The colors were compared with standards and rated as follows:

| 0–1 | colorless-pale yellow | 6–7 | light brown |
|-----|----------------------|-----|-------------|
| 2–3 | pale yellow          | 8–9 | brown       |
| 4–5 | ocher                | 10  | dark brown  |

The test sample was considered to pass if the color unit at the end of 15 minutes was less than 7 units.

What is seen from the above Table is that conventional chlorination processing using a solvent such as carbon tetrachloride or chloroform, (Comparative #G), gives a fairly good quality resins, but also results in some residual carbon tetrachloride, as well as suffering from environmental problems. Emulsion processing, such as shown in Comparative Example H, using water and the solvent as in G, also gave a very good quality resin, but had some residual carbon tetrachloride in the product. Neat processing, such as illustrated by Comparative Example I, which uses no solvents or water, just the wax by itself, requires long reaction times, and higher temperatures, and additionally yields a product which is of poorer quality, but does not contain any residual carbon tetrachloride. Using Process #3 of the invention, results in a product of good quality with no residual carbon tetrachloride in the resin.

Discussion

The instant invention overcomes the prior art problems by essentially reacting a stoichiometric amount of chlorine with the paraffin wax. In this manner, there is no residual chlorine which will act as an organic solvent in excess, and which will need to be removed later. Additionally, there is no emulsion layer between the chlorinated paraffin layer and the aqueous layer, which also increases the final product isoluation costs. An emulsion layer would have been predicted to be formed as evidenced by Example F of the application where the formation of a thick emulsion layer is expressly indicated, which increased the drainage time to about 60 minutes.

Therefore, there are at least two distinguishing features in the invention. First, there is no organic solvent used in the reaction and second, there is no emulsion layer formed. The invention therefore improves over the teachings of the prior art in the elimination of the need for organic solvent removal or excess chlorine removal in addition to the elimination of the formation of an emulsion layer between the aqueous layer and chlorinated paraffin layer, thereby additionally saving costs.

The invention has been described with reference to preferred and alternate embodiments. Obviously, modifications and alterations will occur to others upon the reading and understanding of the specification. It is intended to include all such modifications and alterations insofar as they come within the scope of the appended claims or the equivalents thereof.

What is claimed is:

1. A process for preparing a $C_{14}$–$C_{40}$ chlorinated paraffin having a chlorine content of more than 60% by weight from a $C_{14}$–$C_{40}$ paraffin reactant having less or no chlorine, said process comprising:

reacting the $C_{14}$–$C_{40}$ paraffin reactant with an amount of liquid chlorine which essentially completely reacts with the paraffin to form a chlorinated paraffin phase of said $C_{14}$–$C_{40}$ chlorinated paraffin having a chlorine content of more than 60% by weight, under superatmospheric pressure essentially in the absence of an organic solvent at an elevated temperature ranging up to about 140° C., and in the presence of a free radical forming catalyst, said $C_{14}$–$C_{40}$ paraffin being in intimate mixture with an aqueous phase, the intimate mixture being maintained by stirring, said reacting being continued until a chlorinated paraffin phase and an aqueous hydrochloric acid phase have been formed; and separating said chlorinated paraffin phase from said aqueous phase.

2. The process according to claim 1, wherein said separating step is carried out by cessation of said stirring, and wherein said chlorinated paraffin phase of said $C_{14}$–$C_{40}$ chlorinated paraffin having a chlorine content of more than 60% by weight separates from said aqueous phase.

3. The process according to claim 1, wherein said $C_{14}$–$C_{40}$ paraffin having a lower chlorine content is a paraffin.

4. The process according to claim 1, wherein said $C_{14}$–$C_{40}$ paraffin having a lower chlorine content has been prechlorinated.

5. A process for preparing a highly chlorinated paraffin comprising the steps of:

reacting a $C_{14}$–$C_{40}$ paraffin reactant with an amount of chlorine sufficient to form a chlorinated paraffin phase having a chlorine content of more than 60% by weight, said amount of chlorine essentially completely reacting with said paraffin reactant in the presence of free radical source, under greater than ambient pressure up to about 10 bar, essentially in the absence of an organic solvent at a first temperature up to about 140° C. to maintain said chlorinated paraffin phase as a molten chlorinated paraffin, said molten chlorinated paraffin phase being in intimate mixture with an aqueous phase; and separating said chlorinated paraffin phase from said aqueous phase.

6. The process according to claim 5, wherein said free radical source comprises at least one member selected from the group consisting of free-radical forming catalysts and electromagnetic radiation.

7. The process according to claim 5, wherein said aqueous phase comprises a dilute hydrochloric acid.

8. The process according to claim 5, wherein said first temperature is from about 75 to 140° C. during said reacting step.

9. The process according to claim 5, wherein said first temperature is from about 80 to 105° C. during said reacting step.

10. The process according to claim 5, wherein said pressure ranges up to about 10 bar.

11. The process according to claim 5, wherein said pressure ranges from about 2 to about 6 bar.

12. The process according to claim 5, wherein said aqueous phase is present in an amount sufficient to absorb hydrogen chloride formed during the reaction, or to form a dilute hydrochloric acid having a strength of up to 35% by weight.

13. The process according to claim 5, wherein said reacting step comprises intensive mixing of said intimate mixture, and said separating step further comprises cessation of said intensive mixing.

14. The process according to claim 13, wherein said intensive mixing is performed by stirring.

15. The process according to claim 14, wherein said stirring is performed by an impeller stirrer and said intimate mixture is contained in a reactor having an interior surface, said impeller stirrer being separated from said interior surface by a gap, wherein said gap is small enough to disperse said molten chloroparaffin phase in said aqueous phase when said impeller stirrer stirs said intimate mixture.

16. The process according to claim 5, wherein said paraffin reactant is a hydrocarbon.

17. The process according to claim 5, wherein said paraffin reactant is prechlorinated.

18. The process of claim 5, wherein said paraffin reactant is a $C_{14}$–$C_{40}$ paraffin.

19. The process of claim 5, wherein said phase separation is essentially free of emulsion.

20. The process of claim 5, wherein said separating step comprises maintaining a second temperature above a melting point temperature of said molten chlorinated paraffin phase to effect essentially complete phase separation of said molten chlorinated paraffin phase and said aqueous phase.

* * * * *